United States Patent [19]
Dang et al.

[11] Patent Number: 6,162,937
[45] Date of Patent: Dec. 19, 2000

[54] PROCESS FOR PREPARING CYCLOPENTADIENYL COMPOUNDS

[75] Inventors: Vu Anh Dang, Bear; Lin-Chen Yu, Hockessin, both of Del.; Luigi Resconi, Ferrara, Italy

[73] Assignee: Montell Technology Company B.V., Netherlands

[21] Appl. No.: 09/050,291

[22] Filed: Mar. 30, 1998

[30] Foreign Application Priority Data

Mar. 29, 1997 [EP] European Pat. Off. ............. 97200933

[51] Int. Cl.⁷ ................. C07F 7/30; C07F 7/02; C07F 17/00
[52] U.S. Cl. ............ 556/87; 556/431; 556/466; 556/467; 585/360; 526/160; 526/943; 502/103; 502/117
[58] Field of Search ............... 556/87, 431, 466, 556/467; 585/360

[56] References Cited

U.S. PATENT DOCUMENTS

| | | | |
|---|---|---|---|
| 5,459,117 | 10/1995 | Ewen | 502/117 |
| 5,670,681 | 9/1997 | Kuber | 556/53 |
| 5,945,553 | 8/1999 | Kuber et al. | 556/53 |

FOREIGN PATENT DOCUMENTS

| | | |
|---|---|---|
| 0 512 554 | 11/1992 | European Pat. Off. . |
| 0 512 554 A2 | 11/1992 | European Pat. Off. . |
| 0 516 018 | 12/1992 | European Pat. Off. . |
| 0 516 018 A2 | 12/1992 | European Pat. Off. . |
| 0 722 949 A2 | 7/1996 | European Pat. Off. . |
| 0 722 949 | 8/1996 | European Pat. Off. . |
| 0 751 143 | 1/1997 | European Pat. Off. . |
| 0 751 143 A2 | 1/1997 | European Pat. Off. . |
| 196 37 669 | 3/1998 | Germany . |

OTHER PUBLICATIONS

John A. Ewen, *Makromol. Chem., Macromol, Symp.* 48/49, 253–295 (1991).
Ghera, et al. *J.A.C.S.* vol. 82, pp. 4945–4952 (1960).
Schore, et al. *J.A.C.S.* vol. 106, pp. 7451–7461 (1984).
PCT Application PCT/EP 38–01930 (Jun. 24, 1998).
1991 Makromol. Chem., Macromol. Symp. 48–49, pp. 253–295 **1991 Huthig & Wepf Verlag, Basel.

*Primary Examiner*—Porfirio Nazario-Gonzalez
*Attorney, Agent, or Firm*—Bryan Cave LLP; Maurice B. Stiefel

[57] ABSTRACT

A process for preparing bis-cyclopentadienyl compounds bridged by a methylene group is reported, said process comprising reacting formaldehyde with a cyclopentadienyl compound in the presence of a base and of a solvent having a dielectric constant ($\epsilon$), measured at 25° C., higher than 7. The bridged compounds, obtainable in high yields with this simple single-step process, can be used to prepare ansa-metallocenes, active as catalyst components in the polymerization of olefins.

26 Claims, No Drawings

PROCESS FOR PREPARING CYCLOPENTADIENYL COMPOUNDS

FIELD OF THE INVENTION

The present invention relates to a new and convenient process for the preparation of cyclopentadienyl compounds, and more specifically for the preparation of methylene-bridged bis-cyclopentadienyl compounds.

PRIOR ART DISCLOSURE

Compounds having two cyclopentadienyl rings joined by a structural bridge are known and broadly used in the synthesis of organometallic compounds, mainly for the preparation of ansa-metallocenes which are active as catalyst components in the polymerization of olefins.

In this type of compounds the two cyclopentadienyl groups are generally bridged by divalent radicals having two or more carbon atoms, such as an ethylene group, or with dimethyl-silanediyl groups. There are only a few examples of compounds having two identical cyclopentadienyl groups bridged by a methylene radical and the synthesis thereof involves more than one step and gives unsatisfactory yields.

J. A. Ewen et al. (*Makromol. Chem., Makromol. Symp.* 48/49, 253–295, 1991) describe the preparation of bis(indenyl)methane by addition of a MeLi/ether solution to indene in tetrahydrofurane (THF), followed by careful addition of $CH_2I_2$ in THF, at very low temperatures (−78° C.). The yield is not specified.

The European patent application EP 0 512 554 (Example X) describes the preparation of bis(9-fluorenyl)methane by first adding butyllithium to a fluorene/THF solution and then reacting the obtained fluorenyl lithium salt with $CH_2Cl_2$. Even in this case, the yield is not indicated.

The European patent application EP 0 516 018 describes a process for the preparation of polyolefins having a broad molecular weight distribution by using a catalyst system comprising an aluminoxane and two different zirconocenes. One of the zirconocenes used in Example 18 is rac-methylene-bis(3-t-butyl-1-cyclopentadienyl)zirconium dichloride; even if the synthesis of the corresponding ligand is not described, on page 7 of said application it is reported a reaction scheme for the preparation of one-carbon-bridged metallocenes, comprising reacting a cyclopentadienyl lithium salt with the corresponding fulvene.

U.S. Pat. No. 5,459,117 concerns a broad class of metallocene ligands containing variously substituted cyclopentadienyl rings, where the substituents impart either $C_s$, $C_2$, pseudo-$C_s$ or pseudo-$C_2$ symmetry to the ligand. Although not expressly exemplified, among a plethora of possible ligand structures, the cyclopentadienyl rings can be bridged by a methylene group. In column 14, it is reported a general synthetic scheme for the preparation of said ligands, comprising reacting a cyclopentadienyl anion with a suitably substituted fulvene.

The European patent application EP 0 722 949 describes a process for preparing bis-cyclopentadienyl compounds bridged by a divalent $CR^IR^{II}$ group, wherein $R^I$ is hydrogen or an alkyl radical, and $R^{II}$ is an alkyl or aryl radical. This process comprises the reaction of a ketone or an aldeide of formula $R^IR^{II}CO$, having the desired $R^I$ and $R^{II}$ groups, with a cyclopentadienyl compound, in the presence of a base and of an oxygen-containing solvent having an atomic ratio carbon/oxygen not higher than 3. However, the class of bis-cyclopentadienyl compounds obtainable with this process does not encompass compounds bridged with a methylene group.

The European patent application EP 0 751 143 describes a process for preparing carbon-bridged bis-cyclopentadienyl compounds by reacting, in a two- or more-phases system, one or two cyclopentadienyl compounds with a carbonyl compound in the presence of a base and of a phase-transfer catalyst. Formaldehyde is neither cited among the suitable carbonyl compounds nor used in the working examples.

It would be highly desirable to provide an easy and advantageous route for the preparation of the general class of bis-cyclopentadienyl compounds bridged by a methylene group.

SUMMARY OF THE INVENTION

The applicant has now surprisingly found that, by operating under particular conditions, methylene-bridged bis-cyclopentadienyl compounds can be prepared by means of an easy and conventional one-step process. Therefore, it is an object of the present invention a process for the preparation of bridged bis-cyclopentadienyl compounds of formula (I):

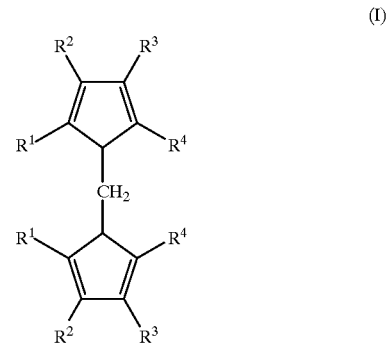

and their double bonds isomers, wherein the substituents $R^1$, $R^2$, $R^3$ and $R^4$, the same or different from each other, are selected from the group consisting of hydrogen, linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl and $C_7$–$C_{20}$-arylalkyl radicals, optionally containing one or more Si and/or Ge atoms; or two or four vicinal substituents $R^1$, $R^2$, $R^3$ and $R^4$ form one or two rings, having from 4 to 8 members, said process comprising reacting formaldehyde with a cyclopentadienyl compound of formula (II):

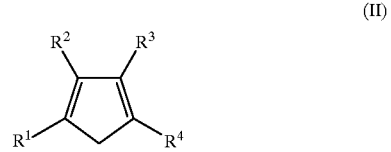

or a double bond isomer thereof, wherein $R^1$, $R^2$, $R^3$ and $R^4$ have the meaning reported above, in the presence of a base, in a solvent having a dielectric constant ($\epsilon$), measured at 25° C., higher than 7.

DETAILED DESCRIPTION OF THE INVENTION

The process according to the present invention will be better described in the following detailed description.

The process according to the present invention allows the obtainment of the compounds of formula (I), or their double bond isomers, starting from the compounds of formula (II), or their double bond isomers, with a rapid and economic one-step reaction, with high yields, avoiding the drawbacks of the processes known in the state of the art. The double bond isomers of the compounds of formulae (I) and (II) can present the double bonds in any of the allowed positions on the cyclopentadienyl rings.

The choice of the reaction solvent is critical in order to obtain the desired final product, in satisfactory yields. The solvent to be used in the process of the present invention have a dielectric constant ($\epsilon$), measured at 25° C., higher than 7, preferably higher than 8, and more preferably higher than 9. Said solvent is preferably selected form the group consisting of dimethyl sulphoxide (DMSO), N,N-dimethylformamide (DMF), sulpholane, N-methylpyrrolidone, N,N-dimethylacetamide, alcohols (such as methanol, ethanol and tert-butanol), tetrahydrofurane (THF), hexamethylphosphoramide and mixtures thereof. More preferably, said solvent is dimethyl sulphoxide or N,N-dimethylformamide.

Furthermore, crown ethers can be added to the above-mentioned solvents, such as 12-crown-4, 15-crown-5 and 18-crown-6.

The process according to the present invention is carried out in the presence of a base; said base is preferably selected from the group consisting of:

alkali or alkali-earth metal hydroxides, such as lithium hydroxide, sodium hydroxide, potassium hydroxide, calcium hydroxide and barium hydroxide;

alkali or alkali-earth metal alcoholates, such as sodium ethylate and potassium tert-butylate;

alkali or alkali-earth metal hydrides, such as sodium hydride and potassium hydride;

alkali or alkali-earth metal alkyls, such as methyllithium and butyllithium;

alkali or alkali-earth metal amides, such as lithium diethylamide;

quaternary ammonium hydroxides or alkoxides, such as tetrabutylammonium hydroxide and tetrabutylammonium ethoxide;

and mixtures thereof.

More preferably, said base is sodium ethylate, potassium hydroxide or potassium tert-butylate.

When the used base is air sensitive, such as potassium hydride or butyllithium, it is suitable to carry out the process of the invention in two steps, i.e. first contacting said base with a cyclopentadienyl compound of formula (II), in order to obtain the corresponding anion, and then adding formaldehyde to the reaction mixture.

Formaldehyde is preferably used in the form of a solution in water (formalin) or in the polymeric form (paraformaldehyde). However, other forms of formaldehyde as well as its solutions at different concentrations can suitably be used.

According to the process of the invention, formaldehyde can be reacted with a cyclopentadienyl compound of formula (II) at any temperature above the melting point of the solvent. The temperature is preferably lower than 100° C., and more preferably comprised between about 0° C. and 50° C. The reaction can suitably be carried out at room temperature.

The reaction time is not limiting, depending to a large extent on the base, solvent and substrate used, on the concentration of the reactants and on the temperature of the reaction.

The molar ratio between the cyclopentadienyl compound (II) and formaldehyde can vary over a wide range; depending on said molar ratio, different embodiments of the process of the invention can be practiced, thus allowing to obtain the desired final products. Each of said embodiments allows the obtainment of a different type of final product. Said above molar ratio is preferably equal to or higher than 2; according to a preferred embodiment of the process of the invention, said molar ratio is 2.

The molar ratio between said base and the cyclopentadienyl compound of formula (II) can vary over a wide range. The process of the invention has the advantage that the base can be used in less than stoichiometric amounts. Said molar ratio base/cyclopentadienyl compound (II) preferably ranges from a catalytic amount to about 2; more preferably from 0.01 to 2, and even more preferably from 0.1 to 1.5.

Depending on the choice of the type and the number of the substituents in the cyclopentadienyl compound of formula (II), different methylene-bridged bis-cyclopentadienyl compounds can be prepared in a single step, with yields much higher than those of the processes known in the state of the art.

Examples of compounds of formula (I) obtainable with the process of the present invention are:

bis(3-methyl-1-cyclopentadienyl)methane,
bis(3-ethyl-1-cyclopentadienyl)methane,
bis(3-isopropyl-1-cyclopentadienyl)methane,
bis(3-t-butyl-1-cyclopentadienyl)methane,
bis(2,4-dimethyl-1-cyclopentadienyl)methane,
bis(2-methyl-4-isopropyl-1-cyclopentadienyl) methane,
bis(2-methyl-4-t-butyl-1-cyclopentadienyl)methane,
bis(2,4-di-t-butyl-1-cyclopentadienyl)methane,
bis(2,3,5-trimethyl-1-cyclopentadienyl)methane,
bis(2,3,5-triethyl-1-cyclopentadienyl)methane,
bis(2,3,4,5-tetramethyl-1-cyclopentadienyl)methane and
bis(2,3,4,5-tetraethyl-1-cyclopentadienyl)methane.

Other advantageous compounds which can be obtained in a single step with the process of the invention, operating at a molar ratio between the cyclopentadienyl compound (II) and formaldehyde of about 2, are methylene-bridged bis-indenyl compounds. These compounds are obtainable by reacting compounds of the formula (II) wherein the substituents $R^1$ and $R^2$, or the substituents $R^3$ and $R^4$ form a benzene ring, that is indenyl or substituted indenyl compounds.

Examples of these bis(indenyl)methane compounds are:

bis(3-indenyl)methane,
bis(1-methyl-3-indenyl)methane,
bis(1-ethyl-3-indenyl)methane,
bis(1-isopropyl-3-indenyl)methane,
bis(1-t-butyl-3-indenyl)methane, bis(4,7-dimethyl-3-indenyl)methane,
bis(2-methyl-3-indenyl)methane,
bis(2-ethyl-3-indenyl)methane,
bis(2-methyl-7-phenyl-3-indenyl)methane,
bis(2-ethyl-7-phenyl-3-indenyl)methane,
bis(2-methyl-7-(1-naphtyl)-3-indenyl)methane,
bis(2-ethyl-7-(1-naphtyl)-3-indenyl)methane,
bis(2-methylacenaphtylindenyl)methane and
bis(2-methyl-4,5-benzoindenyl)methane.

Moreover, substituted bridged bis-cyclopentadienyl compounds of formula (I) can be prepared by a post-treatment of the corresponding unsubstituted or partially substituted compounds, obtained with the process according to the present invention. For example, bis(1-trimethylsilyl-3-indenyl)methane can be obtained by treating the dilithium salt of bis(1-indenyl)methane, obtainable with the process of the invention, with trimethylchlorosilane. Likewise, bis(2-trimethylsilyl-4-t-butyl-1-cyclopentadienyl)methane can be obtained by treating the dilithium salt of bis(3-t-butyl-1-cyclopentadienyl)methane, obtainable with the process of the invention, with trimethylchlorosilane.

Further advantageous compounds obtainable in a single step, carrying out the process according to the present invention, at a molar ratio between the cyclopentadienyl compound (II) and formaldehyde of about 2, are methylene-bridged bis-fluorenyl compounds. These compounds are obtainable by starting from compounds of formula (II) wherein the substituents $R^1$ and $R^2$, and the substituents $R^3$ and $R^4$ form two benzene rings, that is fluorenyl or substituted fluorenyl compounds.

Examples of these bis(fluorenyl)methane compounds are:

bis(9-fluorenyl)methane,
bis(9-(2-t-butylfluorenyl))methane,
bis(9-(2,7-di-t-butylfluorenyl))methane,
bis(9-(2,7-di-t-butyl-4-methylfluorenyl))methane,
bis(9-(1-methylfluorenyl))methane and
bis(9-(3,4-benzofluorenyl))methane.

The bridged cyclopentadienyl compounds obtained from the process of the present invention can be recovered and separated from the reaction mixture by procedures known in the state of the art, such as extraction, crystallization, distillation, chromatography etc.

The methylene-bridged bis-cyclopentadienyl compounds obtainable by the process of the present invention can be used for the preparation of the corresponding metallocene compounds with transition metals such as titanium, zirconium of hafnium, useful as catalytic components in the polymerization of olefins.

The process of the present invention has the advantage of improving the economy of the preparation of the known methylene-bridged bis-cyclopentadienyl compounds; furthermore, said process allows to synthesize new compounds which could not be obtained or could be only hardly obtained, in very low yield and laborious and time consuming procedures according to the processes known in the state of the art.

The following examples are given for illustrative and not limitative purposes.

CHARACTERIZATIONS

All operations were performed under nitrogen by using conventional Schlenk-line techniques. Solvents were purified by degassing with $N_2$ and passing over activated (8 hours, $N_2$ purge, 300° C.) $Al_2O_3$, and stored under nitrogen. MeLi and BuLi (Aldrich) were used as received.

The $^1$H-NMR and $^{13}$C-NMR analysis were carried out on a Varian 300 MHz instrument or on an AC 200 Bruker spectrometer, operating at 200.13 MHz for $^1$H and 50.323 MHz for $^{13}$C; for $^1$H-NMR analysis the solvent was $CDCl_3$, referenced against the peak of residual $CHCl_3$ at 7.25 ppm, or $CD_2Cl_2$, referenced against the peak of residual $CHDCl_2$ at 5.35 ppm; for $^{13}$C-NMR analysis (Broad Band decoupling mode), the solvent was $CDCl_3$, referenced against the central line of $CDCl_3$ at 77.00 ppm. All NMR solvents were dried over $LiAlH_4$ or $CaH_2$ and distilled before use. Preparation of the samples was carried out under nitrogen using standard inert atmosphere techniques.

GC-MS analysis were performed on a HP MS Engine 5989B instrument.

EXAMPLE 1

Synthesis of bis(2,4-di-t-butyl-cyclopentadienyl) methane (a) Synthesis of t-butylcyclopentadiene Methyllithium (1.4 M in ether, 235 mL, 328.4 mmol) was slowly added to a solution of 6,6-dimethylfulvene (31.7 g, 298.6 mmol) in $Et_2O$, at −78° C. The reaction mixture was stirred at room temperature overnight, for 12 hours. The obtained mixture was quenched with water (200 mL), maintained under stirring at room temperature for 1 hour, and finally extracted with $Et_2O$ (3×300 mL). The organic layers were combined, dried over anhydrous magnesium sulphate and filtered; after concentration, a yellow liquid was isolated (36 g; 99% yield). The product, consisting of t-butylcyclopentadiene, was used without any further purification.

(b) Synthesis of 2-butyl-6,6-dimethylfulvene

A mixture of t-butylcyclopentadiene (15 g, 123 mmol), acetone (9.0 mL, 135.2 mmol), pyrrolidine (11.7 mL, 135.3 mmol) and methanol (100 mL) was stirred at 0° C., for 30 minutes, and then at room temperature overnight. The reaction mixture was quenched with acetic acid (7.38 g) and with water (100 mL) at 0° C. The mixture was extracted with $Et_2O$ (3×200 mL); the organic layers were combined, washed with a saturated solution of $NaHCO_3$, dried over anhydrous magnesium sulphate, filtered and finally concentrated, thus yielding 2-butyl-6,6-dimethylfulvene in the form of a yellow liquid (18.24 g, 92% yield).

$^1$HNMR (CDCl$_3$): δ 6.5 (s, 2H), 6.5 (s, 1H), 2.1 (d, 6H) and 1.2 (s, 9H).

(c) Synthesis of di-t-butylcyclopentadiene

Methyllithium (1.4 M in ether, 84.3 mL, 118 mmol) was added to a mixture of 2-butyl-6,6-di-methylfulvene (18.2 g, 112.3 mmol) in $Et_2O$, at −78° C. The reaction mixture then was stirred at room temperature over the weekend. The lithium salt of di-t-butylcyclopentadiene was formed. It was filtered and washed with pentane. The salt then was quenched with water (100 mL) for 1 hour. The mixture was then extracted with $Et_2O$ (3×200 mL); the organic layers were combined, dried over anhydrous magnesium sulphate, filtered and finally concentrated, thus yielding di-t-butylcyclopentadiene as a yellow liquid (72% yield).

$^1$H NMR (CDCl$_3$): δ 6.2, 6.0, and 5.8 (s, 2H); 2.9 (s, 2H), 1.2 (d, 18H).

(d) Synthesis of bis(2,4-di-t-butyl-cyclopentadienyl) methane

Formalin (0.91 g, 112 mmol) was slowly added to a mixture of di-t-butyl-cyclopentadiene (5 g, 280 mmol), NaOEt (0.95 g, 139 mmol) in DMSO (850 mL), at room temperature. After stirring overnight at room temperature, a solution of HCl (1 M, 50 mL) was added. The reaction mixture was extracted with Et$_2$O (2×100 mL); the organic layers were combined, washed with a saturated solution of NaCl and then with water, dried over anhydrous magnesium sulphate, filtered and finally concentrated, thus yielding a brown liquid. Said liquid was heated at 75° C., under a pressure of 1 mmHg, in order to remove the unreacted starting material. The final product was isolated as a viscous brown liquid by Kugelrohr distillation (175° C./1 mmHg), thus obtaining 2.3 g of bis(2,4-di-t-butyl-cyclopentadienyl) methane (56% yield), as confirmed by GC/MS and NMR analyses.

EXAMPLE 2

Synthesis of bis(3-indenyl)methane

Example 2(a)

Formalin (37% solution; 3.5 g, 43.1 mmol) was added to a mixture of indene (10.0 g, 86.2 mmol) and EtONa (2.9 g, 43.1 mmol) in N,N-dimethylformamide (100 mL). The reaction mixture was stirred at room temperature for 12 hours. A solution of HCl (1 M, 50 mL) was added. The mixture was extracted with CH$_2$Cl$_2$ (2×100 mL) and the organic phases combined, washed with a saturated solution of NaCl and then with water, dried over MgSO$_4$, filtered and finally concentrated to yield a viscous brown liquid (89% yield by GC). Vacuum distillation yielded pure bis-(3-indenyl)methane as a yellow viscous oil (b.p. 160–180° C. at 1.2 mmHg, 3.65 g, 35% yield), which can be recrystallized from pentane.

$^1$H NMR (CDCl$_3$, δ, ppm): 7.10–7.60 (m, 8H), 6.25 (s, 2H), 3.85 (s, 2H), 3.40 (s, 4H).

Example 2(b)

1.05 g of EtONa (15.4 mmol) dissolved in 200 mL of DMF and 10.0 ml of indene (90%, 77.5 mmol) were introduced, at room temperature, in this order in a three-neck, 500 mL flask with stirring bar. 3.15 mL of aqueous formalin (37% solution, 38.8 mmol) dissolved in 10 mL of DMF were added dropwise, in 15 minutes: a mildly exothermic reaction was observed and the solution turned dark brown, with shades of violet. At the end of the addition, the reaction mixture was maintained under stirring for 20 hours, at room temperature. The reaction was quenched by pouring the mixture on ice and NH$_4$Cl. The organic product was extracted with Et$_2$O and the water layer was washed with Et$_2$O; the organic layers were combined, dried over MgSO$_4$, filtered and finally concentrated, thus obtaining an orange-brown oil. Said oil was further concentrated to eliminate the remaining indene, thus yielding 9.56 g of bis-(3-indenyl) methane, as an orange-brown oil (53.2% yield by GC).

$^1$H NMR analysis of the final product gave the same results as Example 2(a).

EXAMPLE 3

Synthesis of bis(1-t-butyl-3-indenyl)methane

Example 3(a): With Paraformaldehyde

Paraformaldehyde (0.43 g, 14.3 mmol) was added to a mixture of 3-t-butylindene (4.9 g, 28.6 mmol) and potassium t-butoxide (0.96 g, 8.6 mmol) in dimethylsulphoxide (50 mL). After stirring at room temperature for 12 hours, a solution of HCl (1M, 100 mL) was added. The mixture was extracted with CH$_2$Cl$_2$ (2×100 mL). The organic phases were combined, washed with a saturated solution of NaCl and then with water, dried over anhydrous MgSO$_4$ and finally concentrated, thus yielding the a viscous liquid (4.2 g; yield 82%). Pure bis(1-t-butyl-3-indenyl)methane was separated by column chromatography with hexane as solvent.

$^1$H NMR (CDCl$_3$, δ, ppm): 7.7–7.1 (m, 8H), 6.2 (s, 2H), 3.8 (s, 2H), 3.2 (s, 2H), 1.0 (s, 18 H).

Example 3(b): With Formalin

In a three-neck 1 L flask, provided with stirring bar, were introduced 10.32 g of potassium t-butoxide (92 mmol), dissolved in 400 mL of DMF and 80.6 g of 3-t-butyl-indene (98.2% by GC, 460 mmol). 18.6 mL of aqueous formalin (37% wt., 6.9 g, 230 mmol) were added dropwise over 15 minutes. During the addition, bubbling was not observed, while complete mixing required about 30 minutes. A mildly exothermic reaction was observed and the solution turned to red and finally to dark red. The mixture was maintained under stirring, at room temperature, for 2 hours. The reaction was quenched by pouring the reaction mixture on ice with NH$_4$Cl, extracted with Et$_2$O (2×250 mL), concentrated under reduced pressure to yield an oily orange product; said product crystallized upon standing (about 1 hour), thus giving 83.6 g of a raw product, containing 78.3% wt. of bis(1-t-butyl-3-indenyl)methane (by GC analysis), corresponding to a final yield of 79.9%.

Pure bis(1-t-butyl-3-indenyl)methane may be obtained by extraction of the raw product with pentane ($^1$H NMR analysis corresponds to the one reported in Example 3(a)).

EXAMPLE 4

Synthesis of bis(1-phenyl-5,7-dimethyl-3-indenyl) methane (a) Synthesis of 5,7-dimethylindan-1-one A mixture of 3-chloropropionyl chloride (118.9 g, 0.94 mol) and m-xylene (100 g, 0.94 mol) in CH$_2$Cl$_2$ (200 mL) was added dropwise to AlCl$_3$ (283 g, 2.12 mol), at 0° C. The reaction mixture was then stirred at room temperature for 12 hours. The obtained slurry was poured into a flask containing 1.5 kg of ice. The product was extracted with Et$_2$O (2×800 mL); the organic layers were combined, washed with a saturated solution of NaHCO$_3$ (800 mL) and then water (800 mL), dried over anhydrous MgSO$_4$, filtered and finally concentrated, thus obtaining 175 g of a viscous liquid. The obtained product was used in the next step without further purification.

400 mL of concentrated sulphuric acid was added dropwise to the product obtained as reported above and the solution was heated at 65° C. for 5 hours. The reaction mixture was then cooled to room temperature and slowly poured into a flask containing 2 kg of ice. The mixture was extracted with CH$_2$Cl$_2$ (2×1000 mL); the organic phases were combined, washed with a saturated solution of NaHCO$_3$ and then water, dried over anhydrous MgSO$_4$, filtered and concentrated. The product 5,7-dimethylindan-1-one was isolated by crystallizing from hexane (71.4 g, 47% yield).

$^1$H NMR (CDCl$_3$, δ, ppm): 7.1 (s, 1H), 6.9 (s, 1H), 2.9–3.1 (m, 2H), 2.6–2.7 (m, 2H), 2.55 (s, 3H), 2.4 (s, 3H).

(b) Synthesis of 3-phenyl-4,6-dimethylindene 5,7-Dimethylindan-1-one (13.5 g, 84.4 mmol) in THF (20 mL) was added dropwise to a solution of PhMgBr (3.0 M in Et$_2$O, 63 mL, 188 mmol) at 0° C. The reaction mixture was stirred at room temperature overnight and then was quenched with a saturated solution of ammonium chloride (600 mL). The mixture was extracted with Et$_2$O (2×500 mL); the organic phases were combined, dried over anhydrous MgSO$_4$ and finally concentrated, thus yielding a viscous liquid. The product was used in the next step without further purification.

A mixture of the above product (16 g) and p-toluenesulphonic acid monohydrate (2.6 g) in benzene was heated at reflux for 3 hours. The mixture was cooled to room temperature and then treated with a saturated solution of NaHCO$_3$. The organic layer was washed with water, dried over anhydrous MgSO$_4$, concentrated and finally vacuum distilled, thus yielding 3-phenyl-4,6-dimethylindene (b.p. 120° C. at 0.5 mm Hg, 11.6 g, 78%).

(c) Synthesis of bis(1-phenyl-5,7-dimethyl-3-indenyl) methane (Runs A–D and F, and Comparative Run E)

Paraformaldehyde (68 mg, 2.27 mmol) was added to a mixture of 3-phenyl-4,6-dimethylindene (1.0 g, 4.55 mmol) and EtONa (0.15 g, 2.27 mmol) in dimethylsulphoxide (15 mL), at 25° C. After stirring at room temperature for 4 hours, the reaction mixture was treated with a solution of HCl (1 M, 100 mL). The mixture was extracted with CH$_2$Cl$_2$ (2×100 mL); the organic phases were combined, washed with a saturated solution of NaCl and then with water, dried over anhydrous MgSO$_4$, filtered and finally concentrated to yield a brown viscous liquid. Precipitation in MeOH and filtration yielded the product bis(1-phenyl-5,7-dimethyl-3-indenyl) methane as a solid (0.45 g, 44%).

$^1$H NMR (CDCl$_3$, δ, ppm): 7.7 (m, 14H), 6.25 (s, 2H), 4.5 (s, 2H), 3.8 (s, 2H), 2.35 (s, 6H), 2.0 (s, 6H).

The same experiment was carried out according to the operating conditions reported in Table 1 (runs A–D and F, and comparison run E); the obtained results are reported in Table 1.

EXAMPLE 5

Synthesis of bis(4,7-dimethyl-3-indenyl)methane

Example 5(a): With Paraformaldehyde

Paraformaldehyde (2.08 g, 69.4 mmol) was added to a mixture of 4,7-dimethylindene (25.0 g, 174 mmol) and EtONa (5.9 g, 87 mmol) in dimethylsulphoxide (200 mL) at 25° C. After stirring at room temperature for 12 hours, the reaction mixture was heated at 65° C., for further 8 hours, and was then cooled to room temperature. A solution of HCl (1 M, 400 mL) was added. The mixture was extracted with CH$_2$Cl$_2$ (400 mL); the organic phases combined, washed with a saturated solution of NaCl and then with water, dried with anhydrous MgSO$_4$, filtered and finally concentrated to yield a brown viscous liquid. GC analysis showed only the desired product and part of starting material; no fulvene derivative was detected. Precipitation occurred when the brown liquid was treated with pentane (100 mL). After filtration and washing with pentane and EtOH, bis(4,7-dimethyl-3-indenyl)methane was obtained as a yellow solid. The isolated yield was 33% (6.8 g).

$^1$H NMR (CDCl$_3$, δ, ppm): 6.85–7.05 (m, 4H), 6.35 (s, 2H), 4.20 (s, 2H), 3.2 (s, 4H), 2.55 (s, 6H), 2.35 (s, 6H).

Example 5(b): With Formalin

Formalin (37% aq. solution, 0.28 g, 3.47 mmol) was added to a mixture of 4,7-dimethylindene (1.0 g, 6.94 mmol) and EtONa (0.15 g, 2.20 mmol) in dimethylsulphoxide (10 mL) at 25° C. After stirring at room temperature for 12 hours, the reaction mixture was heated at 80° C. for further 4 hours and then cooled to room temperature. A solution of HCl (1 M, 10 mL) was added. The mixture was extracted with CH$_2$Cl$_2$ (2×50 mL); the organic phases were combined, washed with a saturated solution of NaCl and then with water, dried over anhydrous MgSO$_4$, filtered and finally concentrated to yield a brown solid (GC analysis shows 75% conversion). After washing with MeOH, bis(4,7-dimethyl-3-indenyl)methane was isolated as a yellow solid (0.52 g; yield 50%).

The $^1$H NMR spectrum corresponds to the one of the compound obtained in example 5(a).

EXAMPLE 6

Synthesis of bis(9-fluorenyl)methane

Paraformaldehyde (0.90 g, 30.1 mmol) was added to a mixture of fluorene (10.0 g, 60.2 mmol) and EtONa (2.0 g, 30.1 mmol) in dimethylsulphoxide (100 mL) at 25° C. After stirring at room temperature for 5 hours, the reaction mixture was heated at 90° C. for further 16 hours and then cooled to room temperature. A solution of HCl (1 M, 200 mL) was added. The mixture was extracted with CH$_2$Cl$_2$ (2×250 mL); the organic phases were combined, washed with a saturated solution of NaCl and then with water, dried with anhydrous MgSO$_4$, filtered and finally concentrated. Bis(9-fluorenyl) methane was isolated by precipitation in CH$_3$OH, as a off-white solid (3.52 g, 34% yield).

$^1$H NMR (CDCl$_3$, δ, ppm): 7.2–7.8 (m, 16H), 4.4 (t, 2H, J=7.6 Hz), 2.2 (t, 2H, J=7.6 Hz).

COMPARATIVE EXAMPLE 1

Synthesis of bis(9-fluorenyl)methane Via Dibenzofulvene (a) Synthesis of 9-acetoxymethylfluorene A 250 mL Erlenmeyer flask was charged with 9-fluorenemethanol (30.0 g, 153 mmol, Aldrich), sodium acetate (15.0 g, 183 mmol, Aldrich), and acetic anhydride (0.150 L, 1580 mmol, Aldrich). The reaction mixture was heated over a steam bath, under continuous stirring for 4 hours. The warm mixture was poured into ice (150 g). After reaching room temperature, the solid product was isolated by filtration and washed with cold water. The dried product was used without further purification (35.7 g, 150 mmol, 98% yield, >99% purity by GC).

Mass spectrum (m/e (RA)): 238 (5.6), 178 (100), 165 (41), 43 (44).

(b) Synthesis of Dibenzofulvene

A 1000 mL flask was charged with 9-acetoxymethylfluorene (30.0 g, 126 mmol) and anhydrous petroleum ether (bp 35–60° C., 400 mL, Aldrich) and it was cooled to 5° C. Solid potassium tert-butoxide (16.0 g, 142 mmol, Aldrich) was added in one portion. After stirring for 6 hours, the mixture was poured into dilute HCl (200 mL, 0.1 N). Et$_2$O was added (100 mL); the layers were separated and the product extracted into Et$_2$O (2×100 mL). Combined organic portions were dried over anhydrous MgSO$_4$ and the solvent was removed via rotary evaporation. The crude product dibenzofulvene was isolated as a yellow solid (21.3 g, 94% yield, >99% pure by GC). Further purification was accomplished by recrystallization from petroleum ether, to yield dibenzofulvene in the form of white needles (Tm 51.5–53° C.).

$^1$H NMR (CDCl$_3$, δ, ppm): 7.70 (m, 4H, Ar), 7.30 (m, 4H, Ar), 6.05 (s, 2H, CH$_2$).

(c) Synthesis of bis(9-fluorenyl)methane

A mixture of dibenzofulvene (1 g, 5.68 mmol), fluorene (0.93 g, 5.68 mmol) and EtONa (0.19 g, 2.79 mmol) in DMSO (20 mL) was heated at 90° C. for 16 hours, and was then cooled to room temperature. After carrying out the work-up, as reported in Example 8, 0.55 g of bis(9-fluorenyl)methane were obtained, with a yield of 28%.

The obtained results clearly show that the process according to the present invention allows the obtainment of the desired product with a more convenient and easy process (in only one step) and with higher final yields with respect to the processes known in the art.

COMPARATIVE EXAMPLE 2

Synthesis of bis(9-fluorenyl)methane Via Dichloromethane

A solution of fluorene (3.32 g, 20 mmol) in Et$_2$O (70 mL) was treated with methyllithium (1.4 M solution, 20 mmol, 14.3 mL), at −78° C. When the addition was completed, the temperature of the reaction flask was allowed to rise to room temperature and stirring was maintained overnight. In a separate flask, 10 mmol dichloromethane (0.85 g) were dissolved in 30 mL diethylether and the temperature was lowered to −78° C. The fluorene anion prepared above was added slowly to the stirred solution and the reaction mixture was allowed to warm to room temperature, while being stirred overnight. The reaction was then quenched with dilute HCl; the organic layer was collected, filtered from magnesium sulphate and dried, thus isolating 2.58 g of solid products. GC/MS analysis indicated that only 16% wt. (0.412 g) of the dry products was the target compound.

The obtained results clearly show that the process according to the present invention allows the obtainment of the desired products in much higher yields than the processes known in the art.

EXAMPLE 7

Synthesis of bis(2-methyl-3-indenyl)methane 3.06 g of sodium ethylate (MW 68.05, 45.0 mmol) dissolved in 600 mL of DMF and 30.00 g of 2-methylindene (MW 130.19, 97.6%, 224.9 mmol) were introduced at room temperature in this order in a three neck, 1-L flask with stirring bar. 9.10 mL of aqueous formalin (37%, MW 30.03, 112.1 mmol) were added dropwise: a mildly exothermic reaction was observed and the solution turned dark brown. At the end of the addition, the reaction mixture was maintained under stirring for 2 hours, at room temperature. A final aliquot was taken for GC analysis: 2-methylindene=4.6%, bis(2-methyl-3-indenyl)methane=62.9%, tri-indene byproduct (MW=414)=30.9%. The reaction was quenched by pouring the mixture on ice and NH$_4$Cl. The organic product was extracted with Et$_2$O (3×200 ml) and the water layer was washed with Et$_2$O; the organic layers were combined, washed with water to eliminate the remaining DMF, dried over MgSO$_4$, filtered and finally concentrated, thus obtaining 30.54 g of an orange-brown oil. Said oil was washed with 100 ml pentane and dried again. The final product (12.02 g of white powder) was the crude bis(2-methyl-3-indenyl)methane (GC: product 85.3%, trimer (MW=414)=12.1%)

$^1$H NMR (CDCl$_3$, δ, ppm): 2.15 (s, 6H, CH$_3$); 3.31 (s, CH$_2$, 4H); 3.74 (s, 2H, CH$_2$ bridge); 7.10–7.36 (m, 8H). GC-MS: m/z (%) =272 (M$^+$), 143 (M$^+$ —C$_{10}$H$_9$), 128 (M$^+$ —C$_{11}$H$_{12}$), 115 (C$_9$H$_7^+$).

TABLE 1

| run | aldehyde | amount (mg) | solvent | amount (ml) | base | amount (mg) | temperature (° C.) | time (h) | yield (g) |
|---|---|---|---|---|---|---|---|---|---|
| A | paraformaldehyde | 68 | DMSO | 15 | NaOEt | 150 | 25 | 4 | 44 |
| B | paraformaldehyde | 68 | DMF | 15 | NaOEt | 150 | 25 | 12 | 54 |
| C | formalin | 68 | DMF | 15 | NaOEt | 150 | 25 | 12 | 79 |
| D | formalin | 68 | DMF | 15 | KOH | 150 | 25 | 12 | 58 |
| E (comp.) | formalin | 68 | DME | 15 | KOH | 150 | 25 | 12 | traces |
| F | formalin | 68 | DMF | 15 | NaOEt | 150 | 80 | 6 | 65 |

DMSO = dimethylsulfoxide
DMF = N,N-dimethylformamide
DME = dimethoxyethane

What is claimed is:

1. A process for the preparation of bridged bis-cyclopentadienyl compounds of formula (I):

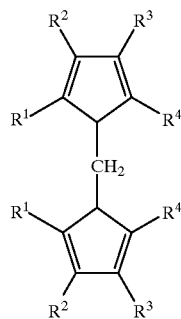

and their double bonds isomers, wherein the substituents $R^1$, $R^2$, $R^3$ and $R^4$, the same or different from each other, are selected from the group consisting of hydrogen, linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl and $C_7$–$C_{20}$-arylalkyl radicals, optionally containing one or more Si and/or Ge atoms; or two or four vicinal substituents $R^1$, $R^2$, $R^3$ and $R^4$ form one or two rings, having from 4 to 8 members, said process comprising reacting formaldehyde with a cyclopentadienyl compound of formula (II):

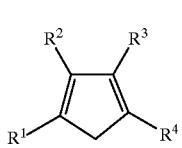

or a double bond isomer thereof, wherein $R^1$, $R^2$, $R^3$ and $R^4$ have the meaning reported above, in the presence of a base, in a solvent having a dielectric constant ($\epsilon$), measured at 25° C., higher than 7, and in the absence of a phase transfer catalyst.

2. The process according to claim 1, wherein said solvent has a dielectric constant ($\epsilon$) higher than 9.

3. The process according to claim 1, wherein said solvent is selected from the group consisting of dimethyl sulphoxide, N,N-dimethylformamide, sulpholane, N-methylpyrrolidone, N,N-dimethylacetamide, methanol, ethanol, tert-butanol, tetrahydrofurane, hexamethylphosphoramide and mixtures thereof.

4. The process according to claim 3, wherein said solvent is dimethyl sulphoxide or N,N-dimethylformamide.

5. The process according to claim 1, wherein said base is selected from the group consisting of alkali and alkali-earth metal hydroxides, alkali and alkali-earth metal alcoholates, alkali and alkali-earth metal hydrides, alkali and alkali-earth metal alkyls, alkali and alkali-earth metal amides, quaternary ammonium hydroxides and alkoxides, and mixtures thereof.

6. The process according to claim 5, wherein said base is sodium ethylate, potassium hydroxide or potassium tert-butylate.

7. The process according to claim 1, wherein formaldehyde is in the form of a water solution (formalin) or in polymeric form paraformaldehyde).

8. The process according to claim 1, wherein the molar ratio between said cyclopentadienyl compound of formula (II) and formaldehyde is 2.

9. The process according to claim 1, wherein the molar ratio between said base and said cyclopentadienyl compound of formula (II) ranges from 0.01 to 2.

10. A process for the preparation of bridged bis-cyclopentadienyl compounds of formula (I):

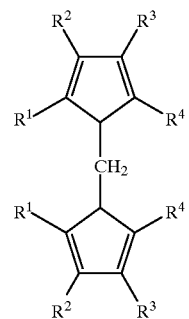

and their double bonds isomers, wherein the substituents $R^1$, $R^2$, $R^3$ and $R^4$, the same or different from each other, are selected from the group consisting of hydrogen, linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl and $C_7$–$C_{20}$-arylalkyl radicals, optionally containing one or more Si and/or Ge atoms; or two or four vicinal substituents $R^1$, $R^2$, $R^3$ and $R^4$ form one or two rings, having from 4 to 8 members, said process consisting essentially of reacting formaldehyde with a cyclopentadienyl compound of formula (II):

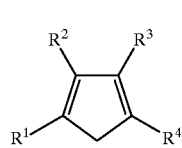

or a double bond isomer thereof, wherein $R^1$, $R^2$, $R^3$ and $R^4$ have the meaning reported above, in the presence of a base, in a solvent having a dielectric constant ($\epsilon$), measured at 25° C., higher than 7, in the absence of a crown ether, and further in the absence of a quaternary ammonium hydroxide.

11. The process according to claim 10, wherein said solvent has a dielectric constant ($\epsilon$) higher than 9.

12. The process according to claim 10, wherein said base is selected from the group consisting of alkali and alkali-earth metal hydroxides, alkali and alkali-earth metal alcoholates, alkali and alkali-earth metal hydrides, alkali and alkali-earth metal alkyls, alkali and alkali-earth metal amides, quaternary ammonium alkoxides, and mixtures thereof.

13. The process according to claim 10, wherein said base is selected from the group consisting of alkali and alkali-earth metal hydroxides, alkali and alkali-earth metal alcoholates, alkali and alkali-earth metal hydrides, alkali and alkali-earth metal alkyls, alkali and alkali earth metal amides, and mixtures thereof.

14. The process according to claim 12, wherein said base is sodium ethylate, potassium hydroxide or potassium tert-butylate.

15. The process according to claim 10, wherein formaldehyde is in the form of a water solution (formalin) or in polymeric form (paraformaldehyde).

16. The process according to claim 10, wherein the molar ratio between said cyclopentadienyl compound of formula (II) and formaldehyde is 2.

17. The process according to claim 10, wherein the molar ratio between said base and said cyclopentadienyl compound of formula (II) ranges from 0.01 to 2.

18. A process for the preparation of bridged bis-cyclopentadienyl compounds of formula (I):

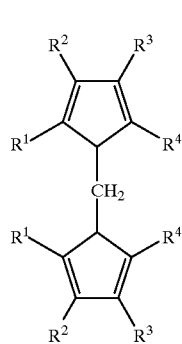

(I)

and their double bonds isomers, wherein the substituents $R^1$, $R^2$, $R^3$ and $R^4$, the same or different from each other, are selected from the group consisting of hydrogen, linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl and $C_7$–$C_{20}$-arylalkyl radicals, optionally containing one or more Si and/or Ge atoms; or two or four vicinal substituents $R^1$, $R^2$, $R^3$ and $R^4$ form one or two rings, having from 4 to 8 members, said process consisting of reacting formaldehyde with a cyclopentadienyl compound of formula (II):

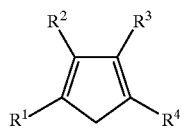

(II)

or a double bond isomer thereof, wherein $R^1$, $R^2$, $R^3$ and $R^4$ have the meaning reported above, in the presence of a base, in a solvent having a dielectric constant ($\epsilon$), measured at 25° C., higher than 7, and in he absence of a quaternary ammonium hydroxide.

19. The process according to claim 18, wherein said solvent has a dielectric constant ($\epsilon$) higher than 9.

20. The process according to claim 18, wherein said base is selected from the group consisting of alkali and alkali-earth metal hydroxides, alkali and alkali-earth metal alcoholates, alkali and alkali-earth metal hydrides, alkali and alkali-earth metal alkyls, alkali and alkali-earth metal amides, quaternary ammonium hydroxides and alkoxides, and mixtures thereof.

21. The process according to claim 18, wherein said base is selected from the group consisting of alkali and alkali-earth metal hydroxides, alkali and alkali-earth metal alcoholates, alkali and alkali-earth metal hydrides, alkali and alkali-earth metal alkyls, alkali and alkali-earth metal amides, quaternary ammonium alkoxides, and mixtures thereof.

22. The process according to claim 18, wherein said base is selected from the group consisting of alkali and alkali-earth metal hydroxides, alkali and alkali-earth metal alcoholates, alkali and alkali-earth metal hydrides, alkali and alkali-earth metal alkyls, alkali and alkali-earth metal amides, and mixtures thereof.

23. The process according to claim 22, wherein said base is sodium ethylate, potassium hydroxide or potassium tert-butylate.

24. The process according to claim 18, wherein formaldehyde is in the form of a water solution (formalin) or in polymeric form (paraformaldehyde).

25. The process according to claim 18, wherein the molar ratio between said cyclopentadienyl compound of formula (II) and formaldehyde is 2.

26. The process according to claim 18, wherein the molar ratio between said base and said cyclopentadienyl compound of formula (II) ranges from 0.01 to 2.

* * * * *